United States Patent [19]

Barer

[11] 4,219,350
[45] * Aug. 26, 1980

[54] 2-ETHYL-1,3-HEXANEDIOL AS A CHEMICAL PINCHING AGENT

[75] Inventor: Sol J. Barer, Clark, N.J.

[73] Assignee: Celanese Corporation, New York, N.Y.

[*] Notice: The portion of the term of this patent subsequent to Sep. 13, 1994, has been disclaimed.

[21] Appl. No.: 934,303

[22] Filed: Aug. 17, 1978

[51] Int. Cl.² .......................... A01N 5/00; A01N 9/24
[52] U.S. Cl. .......................................... 71/78; 71/122; 71/76
[58] Field of Search ............................. 71/78, 122, 76

[56] References Cited

U.S. PATENT DOCUMENTS

| | | | |
|---|---|---|---|
| 3,824,094 | 7/1974 | Tso et al. | 71/78 |
| 3,900,307 | 8/1975 | Abramatis | 71/78 |
| 4,047,925 | 9/1977 | Barer | 71/78 |

OTHER PUBLICATIONS

Chem. Abst. Subject Index-p. 18555cs, 1972–1976–1,3-hexane-diol,-2-ethyl.

Primary Examiner—Catherine L. Mills
Attorney, Agent, or Firm—Kenneth A. Genoni

[57] ABSTRACT

A chemical pruning, and contact composition for the selective inhibition of suckering in plant species subject thereto, particularly tobacco, said composition comprising as an active species 2-ethyl-1,3-hexanediol.

6 Claims, No Drawings

2-ETHYL-1,3-HEXANEDIOL AS A CHEMICAL PINCHING AGENT

BACKGROUND OF THE INVENTION

Certain species of plants exhibit at least in the mature stages a tendency to suckering i.e., the formation of subordinate shoots springing from a bud on the stem, so-called axillary buds. This secondary growth has the effect of subverting the maturation of blossoms, fruit, or leaves for ultimate harvesting and is accordingly desirously avoided in cultivation. This tendency is particularly pronounced in the tobacco plant, especially in the maturation stage following topping or decapitation, i.e., the removal of the terminal growth, main leader or stem apex. In other cases, topping or removal of apical meristematic tissue is itself desirably accomplished chemically.

Large leaf tobaccos as grown in the United States have typically been topped at or shortly after flowering, when dark air cured and fire cured types may have 10 to 16 leaves and burley, flue-cured, Maryland or cigar types may have 16 to 20 leaves. Tops (the blossoms) in tobacco tend to suppress sucker growth down the stalk, so when tops are removed rapid and profuse sucker growth occurs at the juncture of the stem and each leaf thus limiting the development of the upper leaves which are by far the most profitable. Also, suckers provide food for young budworms and hornworms in addition to supplying a preferred site for hornworm egg laying. Accordingly, sucker control is essential for commercial cultivation. It is also important for efficient harvesting, as current mechanical harvesters require near-perfect sucker control for proper operation.

Recently, earlier topping in the button stage has been employed as a means of increasing yields and affording better pest control. The resultant increased tendency to sucker had been controlled in the past by hand removal as often as three times in one season. Most recently, control has been achieved by the use of contact chemical control agents, such as methyl caproate in combination with a later application of a systemic agent such as maleic hydrazide which controls subsequent secondary growths. Successful sucker control permits most of the plant resources to be directed into making larger and heavier leaves, with sufficient spread to have desirable quality.

Various contact chemical agents have been tested for improved sucker control including dimethyldodecylamine acetate ("Penar" manufactured by Pennwalt), 1-octanol/1-decanol mixtures ($C_6$-$C_{12}$) (available, for example as Off-Shoot-T from Proctor and Gamble Co.) the lower alkyl esters of fatty acids (available as Off-Shoot-O from Proctor and Gamble Co.) and Emgard (from Emery Industries, Inc.) and methyl pelargonate (T-61, available from Emery Industries). See *Tobacco Science* XIV, pp. 65–68 (1970) and XVI, pp. 134–135 (1972). Although results of testing vary, the dual use of the higher fatty alcohol/maleic hydrazide systems proved superior in testing as reported in *Tobacco Science* XIV, pp. 86–88 (1970), resulting in the lowest sucker numbers and weight per plant with destruction of the primary and secondary buds in the leaf axils contacted.

A more detailed study of the higher fatty alcohol systems in *J. Agri. Food Chem.* Vol. 15, #16, pp. 972-5 (1967) showed that the $C_9$-$C_{11}$ species were highly active, more so than the corresponding higher fatty acid methyl ester, whereas higher or lower fatty alcohols were relatively inactive.

The higher fatty alcohols and derivatives thereof are in somewhat short supply, and are relatively expensive. Also such systems require the proper type and amount of surfactant to control translocation and avoid nonselective tissue kill.

In addition to the fatty alcohols (U.S. Pat. No. 3,824,094) the lower alkyl esters thereof (U.S. Pat. No. 3,340,040; Canada 968,176) or the combination thereof with an N-carbamate (U.S. Pat. Nos. 3,438,765 and 3,326,664), the patent literature also evidences as chemical pinching agents polyoxyethylene glycol ester mixtures (U.S. Pat. No. 3,985,541); combinations of carboxylic acid diesters of aliphatic glycols, surfactants and aliphatic alcohols of 8 to 12 carbon atoms (U.S. Pat. No 3,900,307); glycol esters of fatty acids (U.S. Pat. No. 3,900,351); combinations of diethylene glycol monobutyl ether and hydrocarbyl ether derivatives (U.S. Pat. No. 3,713,804); and alcohol/glycol esters of styrene-maleic anhydride copolymers (U.S. Pat. Nos. 3,697,250 or 3,556,763) in the last of which there is compared the performance of polyalkylene glycol ethers.

In the case of certain of these chemical agents consequential metabolic changes are induced in the product leaf which are considered to lower the quality of the tobacco. In other cases, there is evidence of undesirable residues being imparted to the leaf. In still further instances, topical application may involve chlorosis, necrosis or distortion of leaf structure, nodal scars or stem burn.

Accordingly, the development of new and improved contact compositions for control of meristematic tissue at reasonable expense is desired, especially for effective control with minimum damage to the cultivar. Commonly assigned U.S. Pat. No. 4,047,925 discloses the use of alkane diols of 2 to 6 carbon atoms and in particular, 1,3-butanediol, as selective suckering inhibitors for various kinds of plants, including tobacco. As noted in this patent, however, other structurally related alkane diols have been found to demonstrate little, if any, effectiveness for this and related uses. It is therefore apparent that no predicatable relationship exists between the chemical structure of a composition and its ability to effectuate to a useful extent pinching and other desirable phytological responses except in the case of a relatively narrowly defined class of substances.

BRIEF DESCRIPTION OF THE INVENTION

It has now been surprisingly discovered that 2-ethyl-1,3-hexanediol which has for its formula $C_3H_7CH(OH)CH(C_2H_5)CH_2OH$ is an effective chemical pruning, pinching or disbudding agent in the control of meristematic tissue and the enhancement of spreading growth in the plant species exhibiting suckering or a growth pattern typically controlled by pruning of meristematic tissue, including tobacco, tomato, azalea. crysanthemum, soybean and cotton. Effective control is achieved with this contact composition in the field without significant plant injury or distortion, i.e., the phytotosis or necrosis in meristematic tissue is essentially selective.

Systems containing this alkane diol are particularly valuable because the active agent 2-ethyl-1,3-hexanediol is water soluble at the concentrations normally used, and is of low toxicity and volatility. Further, control can be achieved even in the absence of a surfactant adjuvant at acceptable levels of phytoxicity.

The remarkable effectiveness of systems containing 2-ethyl-1,3-hexanediol in accordance with this invention is all the more surprising in view of research which shows that such structurally related alkane diols as 1,8-octanediol, 1,9-nonanediol and 1,10-decanediol, for example, exhibit little or no utility in the control of tobacco suckering.

The practice of this invention is represented primarily by the control of suckering in tobacco plants because of its economic significance and for simplicity of description. However, it is found that 2-ethyl-1,3-hexanediol is generally effective in the control of meristematic tissue for plant species requiring such growth control in apical or axillary shoots or buds when applied topically; and no serious adverse effects on plant growth or maturation is seen in other portions of the plant in field tests; or by washing into the soil.

The utilization of 2-ethyl-1,3-hexanediol alone or in combination with other materials is substantially in accordance with art technique as embodied for example in the method of U.S. Pat. No. 2,720,451. As noted above, 2-ethyl-1,3-hexanediol is water soluble and accordingly, can be applied to the plants from aqueous solution with or without a co-solvent, e.g., as a spray, although of course it can also form part of an emulsion system where oily components are included, or can even be included in a paste or foam.

The concentration of the alkane diol in the contact composition should range from an effective amount, generally about 1.0 to 15%, usually about 2 to about 6 by weight for most uses. Concentrates will conveniently incorporate a higher percentage up to high purity 2-ethyl-1,3-hexanediol, but ordinary dilution in conventional spray equipment will result in an ultimate application of an average of about 0.3 to about 15 ml., and preferably about 0.9 to about 9.0 ml., of active alkane diol component to each plant.

Obviously, conditions of application such as temperature, humidity, wind and rain; stage of growth; and plant species will be considered in the individual case. Typically, an aqueous solution of appropriate concentration is prepared and a spray is directed to the top of the plants to the point of runoff. A gallon of spray typically covers about 120 tobacco plants, or expressed otherwise, the coverage represents the application of 20-100 lbs. of active agent per acre of cultivated tobacco. Finer sprays are preferred for foliar application, while a coarse spray will ordinarily be found most useful for contact treatment.

Time of application is related to bud growth and prior manual or chemical pinching if any. Commonly, manual or mechanical pinching or topping is carried out first, followed by chemical pinching at an interval which may range from 1-3 days up to 8 weeks. Where the primary pinching is carried out chemically, application is made just before to just after bud development to insure best results at reasonable concentrations.

In the case of tobacco, which is manually or mechanically topped in the early button or blossoming stage, a spray of 53-66 ml/L 2-ethyl-1,3-hexanediol applied topically to the stem has been found effective in the control of suckers, providing 85-88% control (by weight).

As mentioned earlier, the destruction of apical meristematic tissue tends to stimulate spreading growth by the development of new shoots. In certain species this is a desirable phenomenon and, indeed, the object of the pinching process. Such plants as azaleas or crysanthemums are typical, where control of meristematic tissue leads to spreading growth for better shape or density, and resultant increased blossom profusion.

DETAILED DESCRIPTION OF THE INVENTION 2-ethyl-1,3-hexanediol is a liquid of low toxicity and volatility and can be stored indefinitely without physical, chemical or biological degradation. Concentrates of the diol can be readily prepared, up to the limit of its solubility, in water or in a suitable organic diluent such as a lower alkanol, ethanol being especially preferred. It is, of course, within the scope of this invention to dissolve the diol in an aqueous solution of organic solvent, again, ethanol being preferred. It is understood that mixtures in all proportions of 2-ethyl-1,3-hexanediol in appropriate diluent media are contemplated, and certain of such mixtures may be preferred for selected applications. Commonly, a solution or emulsion of concentrated agent is prepared for dilution with water in a spray device for such purpose. Where surfactant is employed as desired, the spray can actually form a foam of benefit in localizing the agent. It is, of course, possible to admix 2-ethyl-1,3-hexanediol with other agents for sucker control or regulation of meristematic tissue, such as the tertiary or secondary fatty amine, fatty acid ester or fatty alcohol contact agents; or the systemic agents such as maleic hydrazide. Somewhat less conveniently for mass application, the agent can also be provided as a paste or grease as by compounding with soaps or other thickening agents such as silicas, modified clays, etc.

Although the growth control agent of this invention is commonly applied to tobacco after topping, it is also possible to effect simultaneous topping and agent application as by utilizing the Clip-Oil device described in Information Series Bulletin #3, October 1950, Dept. Eng., N.C. Agri. Exp. Station. The agent can be applied, however, within 1-3 days and can be reapplied 10-21 days later as needed. More commonly, the initial chemical pinching is followed within 7-14 days with an application of maleic hydrazide.

The rate of mass application is usually 20 to 100 lbs. per acre of cultivar as an aqueous spray of 5% to 50% growth control agent, or 1.35 to 13.5 ml. per plant. Somewhat greater amounts *up to 2X) are of course involved with foliar application.

2-Ethyl-1,3-hexanediol can be diluted with any essentially inert liquid, and some advantage may be seen in admixtures with the alcohol corresponding to the diol. Where desired, any wetting agent, emulsifier or surfactant may be used. Suitable surfactants may be selected from the anionic, cationic and nonionic types including primary, secondary and tertiary alkyl amines, ethoxylated alcohol sulfates, alkyl sulfates, water soluble salts of a sulfonated alkyl, alkylbenzene, or alkyl glycerol ether, quaternary ammonium salts, quaternary imidazolinium salts, alkyl pyridinium salts, dialkyl morpholinium salts, ethoxylated fatty acids and/or sorbitol esters etc. Preferred are the sorbitan fatty acid esters and the ethoxylated derivatives, ethers of polyoxyethylene glycol, and fatty acid esters of polyethylene glycol.

The amount of surfactant can range from the ordinary low level of 0.1 to 2.0% up to that commonly used with sucker control agents, i.e., 15 to 50% by weight of the active agent.

It is of course also possible to combine the application of sucker control agent with other plant agents including fertilizers, herbicides, fungicides, insecticides, rodenticides, miticides, sterilants, minerals, hormones, pheromones, and like materials commonly used in agriculture for the maintenance of nurture of plant life, or the control of eradication of pests or disease therein, or the presence of undesired species thereabout. In fact, the alkane diol aqueous solution or emulsion may serve as a vehicle for such additives.

In the experimental data which follows, reference is made to contact application, by which is meant the direct contact of the active composition with the tissue for frowth suppression or necrosis as by hand applying to suckers, or dripping agent down the stem. Foliar application refers to a general aerial spray to which the entire surface area of the plant is exposed. Reference to meristematic tissue is inclusive of terminal and axillary buds.

It is understood that the invention has applicability to all tobacco types, including *nicotiana glutinosa, nicotiana tabacum* and *nicotiana rustica* as well as the treatment of other ornamental and agricultural species including herbaceous plants such as ageratum, coleus, cotton, marigold, peanut, snapbean, snapdragon, soybean and tomato; semi-woody plants such as carnation, crysanthemum, forsythia, geranium, hydrangea and poinsetta; and woody plants such as apple, azalea, chamaecyparis, elm, euonymus, juniper, kolkwitzia, ligustrum, lonicera, maple, paper birch, pyracantha, taxus, weigela and pear.

For the preferred tobacco species, it has been observed that the tobacco plant, and particularly the leaves for harvest, are unimpaired in quality, exhibit a high retained filling value, and can be converted to products of excellent aesthetic properties. Further, since the alkane diols are presently in use as humectants on tobacco, no new ingredient is introduced to the smoke chemistry.

EXAMPLE 1

A 75% concentrate of 2-ethyl-1,3-hexanediol was diluted with water to weight concentrations of 3.0, 4.0 and 5.0% of active ingredient. Suckers on sets of field tobacco plants grown in different counties of North Carolina, topped in the button stage immediately prior to treatment, were subjected to a contact spray from a hand held atomizer dribbled down the length of the stem with approximately equal amounts of concentrate being delivered to each plant. The results were compared with a commercial systemic control agent, Off-Shoot T-85, with and without treatment by another commercial systemic control agent, maleic hydrazide. The results are set forth in Table I as follows:

TABLE I

| | | Results of Flue-Cured Tobacco Sucker Control | | | |
|---|---|---|---|---|---|
| | | Number Suckers*/Plant | | Percent Control** | |
| No. | Treatment | Caswell County, N.C. | Johnson County, N.C. | Caswell County, N.C. | Johnson County N.C. |
| 1. | 2-ethyl-1,3-hexanediol 3% | 3.2 | 6.0 | 44 | 21 |
| 2. | 2-ethyl-1,3-hexanediol 4% | 2.0 | 4.6 | 67 | 45 |
| 3. | 2-ethyl-1,3-hexanediol 5% | 1.4 | 2.9 | 79 | 53 |
| 4. | Control-topped, not suckered | 3.4 | 6.6 | 0 | 0 |
| 5. | Off-Shoot-T85 4% (2GPA) | 1.0 | 4.1 | 88 | 42 |
| 6. | Off-Shoot-T85 4% + Royal MH-30 (1.5 GPA) | 3.0 | .6 | 98 | 95 |
| 7. | No. 1 + Royal MH-30 (1.5 GPA) | .1 | .3 | 100 | 95 |
| 8. | No. 2 + Royal MH-30 (1.5 GPA) | 0 | .6 | 100 | 94 |
| 9. | No. 3 + Royal MH-30 (1.5 GPA) | 0 | .3 | 100 | 97 |
| 10. | Royal MH-30 (1.5 GPA) | .2 | 1.8 | 99 | 88 |

*Sucker numbers and percent control are averages of two replications. The data was based on five plants per plot in Caswell County and
**Percent sucker control was determined by dividing the weight of suckers from the control into the difference in weight of suckers from the treatment and control.

Variations are evident in the data summarized in Table I, as a result of the different conditions under which to tobacco plants were grown. However, in all cases 2-ethyl-1,3-hexanediol provided effective suckering control, without significant phytotoxicity especially when combined with treatment by maleic hydrazide. These results were surprising, in that greenhouse testing had shown unacceptable levels of phytotoxicity with useful sucker control.

EXAMPLE 2

Comparison was made between 2-ethyl-1,3-hexanediol and the commercial agent, Off-Shoot T-85, applied to 15 field tobacco plants (variety, Speight G-28) in the early button stage growing in Gainesville Florida. Approximately 30 ml. of concentrate per plant were applied with a three-nozzle boom. Observations were made on the twenty-fifth day following application of the concentrates. The results are set forth in Table II as follows:

TABLE II

| Treatment | | Suckers | | |
|---|---|---|---|---|
| Active Agent | Concentration* | Per Plant | Sucker Weight Per Plant, lbs. | % Sucker Control |
| Topped, not suckered | — | 8 | 1.87 | — |
| 2-ethyl-1,3-hexanediol | 1.5 | 17 | 1.39 | 26 |

TABLE II-continued

| Treatment | | Suckers | | |
|---|---|---|---|---|
| Active Agent | Concen-tration* | Per Plant | Sucker Weight Per Plant, lbs. | % Sucker Control |
| 2-ethyl-1,3-hexanediol | 2.2 | 8 | 1.09 | 42 |
| 2-ethyl-1,3-hexanediol | 3.0 | 11 | 1.43 | 24 |
| 2-ethyl-1,3-hexanediol | 3.8 | 8 | 1.11 | 41 |
| Off-Shoot T-85 | 1.7 | 9 | 0.93 | 50 |
| Off-Shoot T-85 | 2.6 | 9 | 1.02 | 45 |
| Off-Shoot T-85 | 3.4 | 6 | 0.98 | 48 |
| Off-Shoot T-85 | 4.2** | 4 | 0.57 | 70 |

*Concentrations are based on active ingredient. 2-ethyl-1,3-hexanediol was formulated as 75.0% active ingredient and Off-Shoot T-85 as 85% active ingredient. Concentrations of the formulated product were 2, 3, 4 and 5% respectively.
**Slight degree of leaf burn was noted with the highest concentration of these active agents.

This data demonstrated 2-ethyl-1,3-hexanediol to be an effective antisuckering agent, at times approaching the effectiveness of the antisuckering preparation in current use.

EXAMPLE 3

Another comparison field test was carried out comparing 2-ethyl-1,3-hexanediol and Off-Shoot T-85 applied to burley tobacco plants growing in Waynesville, North Carolina approximately 20 mls. of diluted solution were applied to each plant employing a Hydra-Gun. Two replications of twenty plants each were used while the plants were for the most part in early flower, although some of the plants were in full flower. The results are set forth in Table III as follows:

TABLE III

| Compd. | Rate ml/L | Sucker Control, % | Suckers/Pl. | | Weight/ sucker, g. | Leaf | |
|---|---|---|---|---|---|---|---|
| | | | No. | Wt., g | | Injury | Drop |
| Topped, not suckered | — | 00.0 | 5.80 | 258.0 | 44.5 | None | None |
| Off-Shoot T-85 | 46.0 | 92.6 | 0.75 | 19.1 | 24.5 | None | None |
| 2-ethyl-1,3-hexanediol | 39.9 | 67.3 | 4.50 | 84.3 | 18.7 | None | None |
| 2-ethyl-1,3-hexanediol | 53.3 | 84.6 | 3.25 | 39.7 | 12.2 | None | None |
| 2-ethyl-1,3-hexanediol | 66.6 | 87.9 | 2.10 | 31.2 | 14.9 | None | None |

Again, the active antisuckering agent of this invention, 2-ethyl-1,3-hexanediol demonstrated its effectiveness to control suckering in tobacco plants. No injury to the leaf was exhibited by the application of 2-ethyl-1,3-hexanediol a required characteristic of any commercially useful antisuckering agent.

EXAMPLE 4

In a further Example, 2-ethyl-1,3-hexanediol was effective in providing sucker control in flue-cured field tobacco grown in Beltsville, Maryland, where 20 ml of spray solution was applied per plant (ten plants per replicate). At 2 weight percent active ingredient, no control was evidenced, but most suckers were killed with 58% overall control (average of two replicates). Increased levels of additive, while showing control up to 95%, tended to evidence increasing axil necrosis.

Other exemplary aspects of the invention involve particularly treatment of crysanthemum, soybean and cotton plants in the same manner. Constructive compositions comprising combinations of, e.g., higher fatty alcohols and esters thereof and 2-ethyl-1,3-hexanediol in all proportions, are contemplated in aqueous or water-lower alkanol solutions or emulsions. In view of the generally low phytotoxicity of 2-ethyl-1,3-hexanediol in field tests it is expected that effective sucker control agents can be advantageously extended to these materials and at low expense.

What is claimed is:

1. A method for the inhibition of suckering in growing plants susceptible thereto comprising the application of an effective amount of a composition comprising an active agent consisting essentially of 2-ethyl-1,3-hexanediol.

2. The method of claim 1 further comprising applying said composition selectively to the suckering zone.

3. The method of claim 1 wherein the composition comprises an aqueous solution of from about 2.5 to about 50% by weight of 2-ethyl-1,3-hexanediol applied at a rate of from about 0.3 to about 15 ml. per cultivar.

4. A method for the inhibition of secondary growth in growing topped tobacco plants comprising applying topically an effective amount of 2-ethyl-1,3-hexanediol.

5. The method of claim 4, wherein 2-ethyl-1,3-hexanediol is applied in aqueous solution at a concentration from about 2.5 to about 50% by weight and a rate of about 20 to about 100 lbs. per acre of cultivated tobacco.

6. In the inhibition of plant growth by topical application of chemical agent to meristematic tissue, the improvement which comprises the utilization of an effective amount of a composition consisting essentially of 2-ethyl-1-3, hexanediol.

* * * * *